US007405313B2

(12) United States Patent
Vincent

(10) Patent No.: US 7,405,313 B2
(45) Date of Patent: Jul. 29, 2008

(54) METHOD FOR THE SYNTHESIS OF BASIC CHROMIUM CARBOXYLATES

(75) Inventor: John B. Vincent, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 74 days.

(21) Appl. No.: 11/519,883

(22) Filed: Sep. 13, 2006

(65) Prior Publication Data

US 2008/0064894 A1    Mar. 13, 2008

(51) Int. Cl.
    *C07F 7/00*    (2006.01)
(52) U.S. Cl. ........................................................ 556/61
(58) Field of Classification Search ...................... 556/61
    See application file for complete search history.

(56) References Cited

U.S. PATENT DOCUMENTS 3,576,762 A  *  4/1971  Maguet-Martin et al. ... 502/184
5,872,102 A  *  2/1999  Vincent et al. ................ 514/21
6,149,948 A     11/2000 Vincent ...................... 424/655
6,197,816 B1    3/2001  Vincent et al. .............. 514/505
6,444,231 B2    9/2002  Vincent et al. .............. 424/655
6,881,752 B2    4/2005  Vincent et al. .............. 514/505
2008/0033196 A1 * 2/2008 Goh et al. .................... 556/114

OTHER PUBLICATIONS

U.S. Appl. No. 11/519,883, filed Sep. 13, 2006, Vincent.
U.S Appl. No. 11/392,503, filed Mar. 30, 2006, Vincent.

* cited by examiner

*Primary Examiner*—Porfirio Nazario Gonzale
(74) *Attorney, Agent, or Firm*—Oblon, Spivak, McClelland, Maier & Neustadt, P.C.

(57) ABSTRACT

A method for the synthesis of a chromium complex 2, $[Cr_3O(carboxylate)_6(H_2O)_3]^+$ (2), wherein carboxylate is a substituted or unsubstituted C2-C5 alkyl carboxylate, is provided, including the step of:

heating an aqueous reaction mixture of a Cr(III) salt, a substituted or unsubstituted C2-C5 alkyl carboxylic acid and a metal hydroxide for a time period and at a temperature sufficient to generate an aqueous product mixture comprising chromium complex 2 and non-toxic byproducts.

20 Claims, No Drawings

METHOD FOR THE SYNTHESIS OF BASIC CHROMIUM CARBOXYLATES

BACKGROUND OF THE INVENTION

1. Field of Invention

The present invention relates to a method for the synthesis of chromium complexes of formula $[Cr_3O(carboxylate)_6(H_2O)_3]^+$, wherein the synthesis uses simple and inexpensive starting materials and no organic solvents, and can be performed while generating little or no toxic by-products.

2. Discussion of the Background

In the late 1950s and 1960s, rats fed a chromium-deficient diet were found to possess an apparent decreased ability to repress blood glucose concentrations, while chromic ions were shown to increase the efficiency of insulin action in rat epididymal tissue [1-5]. Since these observations, a search has been underway to identify the biologically active form of chromium, that is, the biomolecule which naturally binds chromium (III) and possesses an intrinsic function associated with insulin action in mammals [6-8]. The average American diet contains only about 30 µg Cr per day [9, 10], which has resulted in the development of chromium-containing dietary supplements. Such materials also have potential as insulin-potentiating therapeutics which could possibly see use in the treatment of diabetes and related conditions [11]. Determining the structure, function, and mode of action of the biologically active form of chromium could greatly aid in the rational design of such potential therapeutics.

The first chromium-containing species proposed to be biologically active was glucose tolerance factor(GTF)[1,12]. GTF was first isolated from acid-hydrolyzed porcine kidney powder, although a similar, if not identical, material was subsequently isolated from yeast[1,13]. Currently the term GTF is usually understood to refer to only the material isolated from yeast. GTF is absorbed better than simple chromic salts and potentiates insulin action in rat epididymal tissue or isolated rat adipocytes [14]. However, kinetics studies indicate that GTF does not intrinsically possess biological activity [15]; additionally, the material is apparently a byproduct of the acid hydrolysis step used in its purification [16].

GTF was proposed to be composed of chromic ion, nicotinic acid, and the amino acids glycine, glutamic acid and cysteine [13]. While these results have not been reproducible in some laboratories [17-21], this report stimulated an intense interest in the synthesis of chromic-nicotinate complexes [22-25], some of which have been patented as nutritional supplements. The proposed identification of nicotinic acid (2-carboxypyridine) also stimulated investigations of complexes of chromium(III) with the related pyridine carboxylic acids picolinic acid (2-carboxypyridine) and isonicotinic acid (4-carboxypyridine) [26-28]. As a result chromium(III) tris (picolinate), $Cr(pic)_3$, has become a very popular nutritional supplement and is being tested as a therapeutic for the treatment of symptoms of adult-onset diabetes. It is available over-the-counter in the form of pills, chewing gums, sport drinks, and nutrition bars. $Cr(pic)_3$ has been proposed to be the biologically active form of chromium [29]. This is, however, extremely doubtful given the chemistry required to synthesize this material.

In the last decade, a number of investigators have examined the effects of administering $Cr(pic)_3$ (and in some cases other forms of chromium(III)) to rats on regular diets [30-33]. After an initial preliminary report which suggested beneficial effects on blood variables [30], detailed examinations of the effect of $Cr(pic)_3$ administration in amounts up to 1500 µg/kg diet for up to 24 weeks have found no acute toxic effects [31-33]. However, the compound and other chromium sources examined (most notably "Cr nicotinate" and chromium chloride) also had no effect on body mass, percentage lean or fat content, tissue size (heart, testes, liver, kidney, muscle, epididymal fat, spleen, and kidney), or blood variables (fasting glucose, insulin, cholesterol, etc.). No differences in the gross histology of the liver or kidney (organs where chromium(III) preferentially accumulated) were found, although chromium did accumulate in these organs [33]. Another study compared the effects of a Cr-deficient diet with diets supplemented with ten different sources of chromium, including allowing rats to live in stainless steel cages. The Cr sources had no effect on body mass; all but one source decreased epididymal fat. Testes and liver masses tended to be lowered, whereas kidney, heart, and spleen masses were not significantly altered. Supplemental Cr had no effect on serum triglycerides or cholesterol, and only one source resulted in lower serum glucose [34]. While these studies did not manifest any acute toxicity, the lack of beneficial effects of $Cr(pic)_3$ supplementation on growth, fat content or glucose, insulin, or cholesterol concentrations raises questions about its therapeutic potential. Recently the safety of intaking $Cr(pic)_3$ has been questioned, especially in regards to its potential to cause clastogenic damage [35,36]. At physiologically-relevant concentrations of chromium (120 nM) and biological reductants such as ascorbic acid and thiols (5 mM), $Cr(pic)_3$ has been shown to catalytically produce hydroxyl radicals which cleave DNA[35]. This ability stems from the combination of chromium and picolinate; the picolinate ligands prime the redox potential of the chromic center such that it is susceptible to reduction. The reduced chromium species interacts with dioxygen to produce reduced oxygen species including hydroxyl radical. These studies are in agreement with earlier studies which showed that mutagenic forms of chromium(III) required chelating ligands containing pyridine-type nitrogens coordinated to the metal [37].

Cr3 and other compounds of the general formula $[Cr_3O(O_2CR)_6L_3]^{n+}$ (where M is a trivalent transition metal ion, R is an organic group, and L is a terminal ligand such as water or pyridine) are called basic chromium carboxylates. [For Cr3, R=Et, L=$H_2O$, and n=1 Complex 1]. They historically have been prepared by "three general methods: reaction of freshly precipitated chromium(III) hydroxide with the carboxylic acid, either neat or in aqueous solution; reduction of chromium trioxide in the acid media, the reductant being the acid itself (acetic or formic), or some added substance such as ethanol; and oxidation of chromium(II) carboxylates." [38] In terms of synthesizing Cr3 or any of these on an industrial scale, all of these avenues are problematic. Cr(II) compounds are air sensitive and would require specialized equipment. Chromium trioxide and other Cr(VI) complexes are carcinogenic; the possibility of incomplete reduction could represent a health risk. Freshly prepared chromic hydroxide is a very fine powder, which is very difficult to filter on a laboratory scale and should be extraordinarily difficult to filter to isolate on an industrial scale. Additionally, the filtrate, which could potentially be recycled to some degree, is an extremely caustic solution.

For Cr3 specifically, a few syntheses have been described in the literature. The first reported synthesis of Cr3 dates back to 1908 by A. Werner [39]; Werner started from chromic hydroxide, although the formula for the chloride salt of Cr3 was incorrectly reported as $[Cr_3(OH)_2(propionate)_6]$ Cl.5$H_2O$, although this is remarkably close to the correct $[Cr_3O(propionate)_6(H_2O)_3]Cl.(H_2O)_n$, especially given the resources available at the time. Weinland and Hoehn apparently also made Cr3 from Cr(VI) in 1911 [40]. Another reported synthesis of Cr3 in English appeared in 1966 by Earnshaw and coworkers, although the cation was still incorrectly identified as $[Cr_3(OH)_2(propionate)_6]^+$ [41]. They basically used the chromic hydroxide procedure of Werner. The use of chromic hydroxide to generate Cr3 was also reported by Szymanska-Buzar and Ziolowski [42]; their procedure was a simple variation on that of Werner. Kapoor and Sharma [43] reported synthesizing Cr3 from anhydrous $CrCl_3$ and propionic acid in $CCl_4$, starting at −10° C. and then heating the reaction to reflux with the generation of HCl. The use of an organic solvent, especially a carcinogen, is less than ideal, as is the generation of HCl. Antsyshkina and coworkers [44] prepared Cr3 by heating a mixture of chromium nitrate and propionic anhydride; the mixture was heated until toxic, noxious fumes of nitrogen oxide, $NO_x$, appeared. Finally, following the procedure developed by Vincent and coworkers for making basic chromium carboxylates in nonaqueous solvents [45], Fujihara, et al. [46] prepared Cr3 from chromium nitrate and propionic acid in acetone.

Thus, all synthetic procedures for preparing Cr3 to date involve the use of nonaqueous solvents, the formation difficult to isolate chromic hydroxide as an intermediate, or the production of toxic or hazardous byproducts. A one-pot, aqueous synthesis of Cr3 and related complexes without the production of toxic byproducts, which can be scaled from the laboratory to an industrial setting, is needed.

REFERENCES

1. Schwarz K, Mertz W (1959) Arch Biochem Biophys 85: 292.
2. Mertz W, Schwarz K (1959) J Physiol 196: 614.
3. Mertz W, Roginski E E, Schwarz K (1961) J Biol Chem 236: 318.
4. Mertz W, Roginski E E (1963) J Biol Chem 238: 868.
5. Mertz W, Roginski E E, Schroeder H A (1965) J Nutr 86: 107.
6. Davis C M, Vincent J B (1997) J Biol Inorg Chem 2: 675.
7. Vincent J B (1999) J Am Coll Nutr 18: 6.
8. Lukaski H C (1999) Ann. Rev. Nutr. 19: 279.
9. Anderson R A, Koziovsky A S (1985) Am J Clin Nutr 41: 768.
10. Anderson R A (1994) In: Mertz W, Abernathy C O, Olin S S (eds) Risk Assessment of Essential Elements. ISLI Press, Washington, pp. 187-196.
11. Anderson R A (1998) J Am Coll Nutr 17: 548.
12. Schwarz K, Mertz W (1957) Arch Biochem Biophys 72: 515.
13. Toepfer E W, Mertz W, Polansky M M, Roginski W W, Wolf W R (1977) J Agric Food Chem 25: 162.
14. Anderson R A, Brantner J H, Polansky M M (1998) J Agric Food Chem 26: 1219.
15. Vincent J B (1994) J Nutr 124: 117.
16. Sumrall K K. Vincent J B (1997) Polyhedron 16: 4171.
17. Gonzalez-Vergara E, Hegenauer J, Saltman P (1982) Fed Proc 41: 286.
18. Haylock S J, Buckley P D, Blackwell L F (1983) J Inorg Biochem 18: 195.
19. Mirsky N, Weiss A, Dori Z (1980) J Inorg Biochem 13: 11.
20. Kumpulainen J, Koivistoinen P, Lahtinen S (1978) Bioinorg Chem 8: 419.
21. Votava H J, Hahn C J, Evans G W (1973) Biochem Biophys Res Commun 55: 312.
22. Gonzalez-Vergara E, Hegenauer J, Saltman P, Sabat M, Ibers J A (1982) Inorg Chim Acta 66: 115.
23. Gerdom L E, Goff E M (1982) Inorg Chem 21: 3847.
24. Chang J C, Gerdom L E, Baenziger N C, Goff H M (1983) Inorg Chem 22: 1739.
25. Cooper J A, Anderson B F, Buckley P D, Blackwell L F (1984) Inorg Chim Acta 91: 1.
26. Bradshaw J E, Grossie D A, Mullica D F, Pennington D E (1988) Inorg Chim Acta 141: 41.
27. Steams D M, Armstrong W H (1992) Inorg Chem 31: 5178.
28. Evans G W, Pouchnik D J (1993) J Inorg Biochem 49: 177.
29. Evans G W, Bowman T D (1992) J Inorg Biochem 46: 243.
30. Evans G W, Meyer L (1992) Age 15: 134.
31. Hasten D L, Hegsted N L Keenan M J, Morris G S (1997) Nutr Res 17: 283.
32. Hasten D L, Hegsted M. Keenan M J, Morris G S (1997) Nutr Res 17: 1175.
33. Anderson R A, Bryden N A, Polansky M M (1997) J Am Coll Nutr 6:273.
34. Anderson R A, Bryden N A, Polansky M M, Gautschi K (1996) J Trace Elem Exp Med 9:11.
35. Speetjens J K, Collins R A, Vincent J B, Woski S A (1999) Chem Res Toxicol, 12:483.
36. Stearns D M, Belbruno J J, Wetterhahn K E (1995) FASEB J 9: 1650.
37. Sugden K D, Geer R D, Rogers S J (1992) Biochemistry 31: 11626.
38. Cannon, R. D.; White, R. P. Prog. Inorg. Chem. 1988, 36, 195-297.
39. Werner, A. Berichte der Deutschen Chemischen Gesellschaft 1908, 41, 3447-3465.
40. Weinland, R. F.; Hoehn, K. Z. Anorg. Chem. 1911, 69, 158-178.
41. Earnshaw, A.; Figgis, B. N.; Lweis, J. J. Chem. Soc. (A) 1966, 1656-1663.
42. Szymanska-Buzar, T.; Ziolkowski, J. J. Sov. J. Coord. Chem. 1976, 2, 897-912.
43. Kapoor, R.; Sharma, R. Z. Naturforsch. 1979, 34B, 1369-1372.
44. Antsyshkina, A. S.; Porai-Koshits, M. A.; Arkhangel'skii, I. V.; Diallo, I. N. Russ. J. Inorg. Chem. 1987, 32, 1700-1702.
45. Harton, A.; Nagi, M. K.; Glass, M. M.; Junk, P. C.; Atwood, J. L.; Vincent, J. B. Inorg. Chim. Acta 1994, 217, 171-179.
46. Fujihara, T.; Aonahata, J.; Kumakura, S.; Nagasawa, A.; Murakami, K.; Ino, T. Inorg. Chem. 1998, 37, 3779-3784.

SUMMARY OF THE INVENTION

Accordingly, one object of the present invention is to provide a method for synthesis of chromium complex 2 $[Cr_3O(carboxylate)_6(H_2O)_3]^+$ (2), which is readily scaled to industrial scale and produces little or no toxic by-products.

A further object of the present invention is to provide a method for synthesis of chromium complex 2 that uses no organic solvents and uses simple and inexpensive starting materials.

A further object of the present invention is to provide a method for synthesis of chromium complex 2 that can be performed in one pot, in essentially one step. These and further objects of the present invention have been satisfied, either individually or in combinations, by the discovery of a method for the synthesis of a chromium complex 2, $[Cr_3O (carboxylate)_6(H_2O)_3]^+$ (2), wherein carboxylate is a substituted or unsubstituted C2-C5 alkyl carboxylate, comprising:

heating an aqueous reaction mixture of a Cr(III) salt, a substituted or unsubstituted C2-C5 alkyl carboxylic acid and a metal hydroxide for a time period and at a temperature sufficient to generate an aqueous product mixture comprising chromium complex 2 and non-toxic byproducts.

DETAILED DESCRIPTION OF THE INVENTION

The present invention relates to a method for synthesis of chromium complex 2, $[Cr_3O(carboxylate)_6(H_2O)_3]^+$ (2), wherein carboxylate is a substituted or unsubstituted C2-5 alkyl carboxylate. Preferably the carboxylate group is acetic, propionic, n-butyric or n-pentanoic, most preferably propionic (thus resulting in Complex 1, $[Cr_3O(O_2CCH_2CH_3)_6(H_2O)_3]^+$, noted above, called Cr3).

Complex 1 has been shown in healthy and model type 2 diabetic rats to increase insulin sensitivity and improve blood plasma cholesterol and triglycerides levels and to reduce glycated hemoglobin in the diabetes models. Complex 1 has also been shown to reduce the onset of colorectal cancer in rat. Complex 1 is absorbed very rapidly and very efficiently compared to other chromium-containing nutritional supplements. It also dissolves in water very rapidly.

In the method of the present invention, a chromium(III) salt [such as $CrCl_3 \cdot 6H_2O$], a substituted or unsubstituted C2-C5 alkyl carboxylic acid, sodium hydroxide and water (or an aqueous solution of the last two) are combined in a reaction vessel. This is preferably heated under reflux conditions until a dark green color develops. Allowing the solution to cool produces a green solid or oil of the corresponding salt of the chromium complex 2, which is isolated by filtration or by decanting the solution above the oil. The filtrate is a dark blue solution comprised of other chromium carboxylate complexes, water, carboxylic acid, and sodium chloride. This material, comprised of harmless byproducts, can be recycled to subsequent reaction mixtures to obtain more yield of the chromium complex 2.

Alternatively, addition of water to the reaction product before filtration or decanting yields a solution, primarily of chromium complex 2, which can be used without filtration or decanting as a liquid form of the chromium complex 2, particularly for feed supplement applications such as spraying into animal feed, etc.

The balanced reaction is

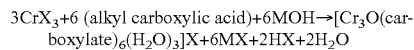

where X, M and alkyl carboxylic acid are as described below.

In the present method, the chromium (III) salt can be any Cr(III) salt. In particular, in the balanced reaction above, X is an anion, which when combined with the metal M of the hydroxide source in the reaction, generates a water-soluble MX compound. Preferably X is halogen, substituted or unsubstituted C2-C5 alkyl carboxylate (wherein the substituents can be selected from the same substituents described below for the alkyl carboxylic acid component).

M is a metal cation, which when combined with a hydroxide anion, generates a water-soluble metal hydroxide. Preferably, M is an alkali metal or alkaline earth metal, more preferably sodium or potassium or calcium, most preferably sodium.

The alkyl carboxylic acid is any unsubstituted C2-C5 alkyl carboxylic acid or substituted C2-C5 alkyl carboxylate. Suitable substituents are any substituent that does not interfere with the reaction to provide the basic chromium complex, including but not limited to, C1-C4 alkoxy, and halogen. Preferably the alkyl carboxylic acid is acetic acid, propionic acid, n-butyric acid or n-pentanoic acid, most preferably propionic acid. These acids would respectively result in the chromium complex 2 wherein the carboxylate group is, respectively, acetic, propionic, n-butyric or n-pentanoic, most preferably propionic.

Although the balanced reaction stated above indicates particular molar ratios of starting materials (i.e. 1:2:2 Cr(III) salt:alkyl carboxylic acid:metal hydroxide), the molar ratios can vary as desired in order to achieve optimum reaction. Preferably the molar ratio of Cr(III) salt to alkyl carboxylic acid is in a range of from 1:2 to 1:100, most preferably 1:2. Preferably the molar ratio of Cr(III) salt to metal hydroxide is in a range of from 1:2 to 1:3, most preferably 1:2. The reaction mixture is aqueous with the Cr(III) salt being present in a molar concentration of from 1-3 molar, based on the amount of water in the mixture. The other starting materials are adjusted according to the desired ratios relative to Cr(III) salt.

The reaction is performed for a time period and at a temperature sufficient to produce the chromium complex 2, the production of which is signified by a color change in the reaction mixture from a blue-green/green-blue color to a dark green color. Preferably the time period is from 10 minutes to 3 hours. The temperature is generally the reflux temperature of the reaction mixture. In the case of aqueous mixtures, this is generally within about 10° C. of 100° C. (the boiling point of water). However, it is also possible to conduct the reaction at temperatures below the reflux temperature, provided that the reaction time is increased to permit reaction to go to completion. Accordingly, temperatures from 35° C. to reflux of the solution can be used, preferably 40° C. to reflux, more preferably 50° C. to reflux, most preferably within 10° C. of the reflux temperature of the solution.

Having generally described this invention, a further understanding can be obtained by reference to certain specific examples which are provided herein for purposes of illustration only and are not intended to be limiting unless otherwise specified.

EXAMPLE 13.00 g (0.04879 moles) $CrCl_3 \cdot 6H_2O$, 10.00 mL propionic acid (0.134 moles), 4.01 g (0.100 moles) NaOH, and 24.0 mL $H_2O$ are added in order to a round bottom flask equipped with a magnetic stir bar. The mixture is heated to reflux with stirring for ~2 hours and 15 minutes. The product was allowed to cool to room temperature and sit until precipitation of a dark green solid is complete. The reaction mixture is then filtered to give a dark green crystalline solid of the chloride salt of Cr3 (>6.7 grams, >55% yield).

This application is related to U.S. Pat. Nos. 5,872,102; 6,149,948; 6,197,816 and 6,444,231, and pending U.S. patent application Ser. No. 11/392,503, the entire contents of each of which are hereby incorporated by reference.

Obviously, additional modifications and variations of the present invention are possible in light of the above teachings. It is therefore to be understood that within the scope of the appended claims, the invention may be practiced otherwise than as specifically described herein.

The invention claimed is:

1. A method for the synthesis of a chromium complex 2, $[Cr_3O(carboxylate)_6(H_2O)_3]^+$ (2), wherein carboxylate is a substituted or unsubstituted C2-C5 alkyl carboxylate, comprising:

heating an aqueous reaction mixture of a Cr(III) salt, a substituted or unsubstituted C2-C5 alkyl carboxylic acid and a metal hydroxide for a time period and at a temperature sufficient to generate an aqueous product mixture comprising chromium complex 2 and non-toxic byproducts.

2. The method of claim 1, further comprising separating the chromium complex 2 from the aqueous product mixture.

3. The method of claim 2, wherein the separating is performed by filtration or decanting.

4. The method of claim 1, wherein carboxylate is a member selected from the group consisting of acetate, propionate, n-butyrate and n-pentanoate.

5. The method of claim 4, wherein carboxylate is acetate or propionate.

6. The method of claim 5, wherein carboxylate is propionate.

7. The method of claim 1, wherein the Cr(III) salt is $CrCl_3 \cdot 6H_2O$.

8. The method of claim 6, wherein the Cr(III) salt is $CrCl_3 \cdot 6H_2O$.

9. The method of claim 1, wherein the metal of the metal hydroxide is an alkali metal or alkaline earth metal.

10. The method of claim 9, wherein the metal of the metal hydroxide is sodium, potassium or calcium.

11. The method of claim 10, wherein the metal of the metal hydroxide is sodium.

12. The method of claim 8, wherein the metal of the metal hydroxide is sodium.

13. The method of claim 1, wherein the molar ratio of Cr(III) salt:alkyl carboxylic acid is in a range from 1:2 to 1:100.

14. The method of claim 13, wherein the molar ratio of Cr(III) salt:alkyl carboxylic acid is approximately 1:2.

15. The method of claim 1, wherein the molar ratio of Cr(III) salt:metal hydroxide is in a range from 1:2 to 1:3.

16. The method of claim 15, wherein the molar ratio of Cr(III) salt:metal hydroxide is approximately 1:2.

17. The method of claim 1, wherein the molar ratios of Cr(III) salt:alkyl carboxylic acid:metal hydroxide are in a range from 1:2:2 to 1:3:100.

18. The method of claim 17, wherein the molar ratios of Cr(III) salt:alkyl carboxylic acid:metal hydroxide are approximately 1:2:2.

19. The method of claim 12, wherein the molar ratios of $CrCl_3 \cdot 6H_2O$:propionic acid:sodium hydroxide are in a range from 1:2:2 to 1:3:100.

20. The method of claim 19, wherein the molar ratios of $CrCl_3 \cdot 6H_2O$:propionic acid:sodium hydroxide are approximately 1:2:2.

* * * * *